US009241768B2

(12) United States Patent (10) Patent No.: US 9,241,768 B2
Sandhu et al. (45) Date of Patent: Jan. 26, 2016

(54) INTELLIGENT INPUT DEVICE CONTROLLER FOR A ROBOTIC CATHETER SYSTEM

(75) Inventors: Kulbir S. Sandhu, Fremont, CA (US); Devanshi Shah, Santa Clara, CA (US); Venkata Adusumilli, Santa Clara, CA (US); John A. Hauck, Shoreview, MN (US); Eric S. Olson, Maplewood, MN (US); Mark B. Kirschenman, Waverly, MN (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 471 days.

(21) Appl. No.: 12/964,407

(22) Filed: Dec. 9, 2010

(65) Prior Publication Data

US 2011/0144806 A1 Jun. 16, 2011

Related U.S. Application Data

(63) Continuation-in-part of application No. 12/751,843, filed on Mar. 31, 2010, which is a continuation-in-part of application No. 12/347,811, filed on Dec. 31, 2008, now Pat. No. 8,343,096.

(60) Provisional application No. 61/040,143, filed on Mar. 27, 2008, provisional application No. 61/099,904, filed on Sep. 24, 2008.

(51) Int. Cl.
*A61B 19/00* (2006.01)
*A61B 17/00* (2006.01)

(52) U.S. Cl.
CPC ......... *A61B 19/2203* (2013.01); *A61B 19/5244* (2013.01); *A61B 19/56* (2013.01);

(Continued)

(58) Field of Classification Search
CPC ............... A61B 19/5244; A61B 19/56; A61B 2019/2211; A61B 19/2203; A61B 2017/003
USPC ....................................... 604/95.01, 500, 508
See application file for complete search history.

(56) References Cited

U.S. PATENT DOCUMENTS 3,091,130 A 5/1963 Payerle et al.
3,605,725 A 9/1971 Bentov (Continued)

FOREIGN PATENT DOCUMENTS

EP 0151479 8/1985
EP 09094796 3/1999

(Continued)

OTHER PUBLICATIONS

"International Search Report & Written Opinion", PCT/US2009/069712 Feb. 25, 2010.

(Continued)

*Primary Examiner* — Nicholas Lucchesi
*Assistant Examiner* — Melissa A Snyder
(74) *Attorney, Agent, or Firm* — Dykema Gossett PLLC

(57) ABSTRACT

A robotic catheter system includes a robotic controller; a robotic manipulator; and in input controller. The input controller includes communication circuitry configured to receive a signal from a user input device; memory having stored therein a plurality of device drivers associated with a different type of input device or a differently configured input device; and a processor configured to recognize an input device connected with the communications circuitry, load a device driver according to the recognized input device, initialize the input device, and/or one of reject and notify an end user, and deliver an image to a display or graphical user interface.

17 Claims, 13 Drawing Sheets

(52) U.S. Cl.
CPC .............. *A61B2017/00026* (2013.01); *A61B 2019/2211* (2013.01); *A61B 2019/2223* (2013.01); *A61B 2019/2234* (2013.01); *A61B 2019/2242* (2013.01); *A61B 2019/2273* (2013.01); *A61B 2019/2276* (2013.01); *A61B 2019/2292* (2013.01); *A61B 2019/464* (2013.01); *A61B 2019/507* (2013.01)

(56) References Cited

U.S. PATENT DOCUMENTS

| | | | |
|---|---|---|---|
| 3,893,449 A | 7/1975 | Lee et al. | |
| 4,160,508 A | 7/1979 | Frosch et al. | |
| 4,348,556 A | 9/1982 | Gettig et al. | |
| 4,393,728 A | 7/1983 | Larson et al. | |
| 4,543,090 A | 9/1985 | McCoy | |
| 4,758,222 A | 7/1988 | McCoy | |
| 4,784,042 A | 11/1988 | Paynter | |
| 4,802,487 A | 2/1989 | Martin et al. | |
| 4,884,557 A | 12/1989 | Takehana et al. | |
| 4,962,448 A | 10/1990 | DeMaio et al. | |
| 4,974,151 A * | 11/1990 | Advani et al. | 710/8 |
| 5,078,140 A | 1/1992 | Kwoh | |
| 5,107,080 A | 4/1992 | Rosen et al. | |
| 5,170,817 A | 12/1992 | Sunderland et al. | |
| 5,238,005 A | 8/1993 | Imran | |
| 5,298,930 A | 3/1994 | Asakura | |
| 5,303,148 A | 4/1994 | Mattson | |
| 5,318,525 A | 6/1994 | West et al. | |
| 5,339,799 A | 8/1994 | Kami et al. | |
| 5,396,266 A | 3/1995 | Brimhall et al. | |
| 5,410,638 A | 4/1995 | Colgate et al. | |
| 5,441,483 A | 8/1995 | Avitall | |
| 5,449,345 A * | 9/1995 | Taylor et al. | 604/100.03 |
| 5,520,644 A | 5/1996 | Imran | |
| 5,533,967 A | 7/1996 | Imran | |
| 5,545,200 A | 8/1996 | West et al. | |
| 5,579,442 A | 11/1996 | Kimoto et al. | |
| 5,607,158 A | 3/1997 | Chan | |
| 5,607,462 A | 3/1997 | Imran | |
| 5,623,582 A | 4/1997 | Rosenberg | |
| 5,630,783 A | 5/1997 | Steinberg | |
| 5,661,253 A | 8/1997 | Aoki | |
| 5,706,827 A | 1/1998 | Ehr et al. | |
| 5,784,542 A | 7/1998 | Ohm et al. | |
| 5,791,908 A | 8/1998 | Gillio | |
| 5,800,178 A | 9/1998 | Gillio | |
| 5,807,377 A | 9/1998 | Madhani et al. | |
| 5,808,665 A | 9/1998 | Green | |
| 5,828,813 A | 10/1998 | Ohm | |
| 5,854,622 A | 12/1998 | Brannon | |
| 5,861,024 A | 1/1999 | Rashidi | |
| 5,876,325 A | 3/1999 | Mizuno et al. | |
| 5,897,488 A | 4/1999 | Ueda | |
| 5,913,820 A | 6/1999 | Bladen | |
| 6,040,758 A | 3/2000 | Sedor et al. | |
| 6,063,095 A | 5/2000 | Wang et al. | |
| 6,113,395 A | 9/2000 | Hon | |
| 6,201,196 B1 | 3/2001 | Wergen | |
| 6,233,476 B1 | 5/2001 | Strommer | |
| 6,233,504 B1 | 5/2001 | Das et al. | |
| 6,290,683 B1 | 9/2001 | Erez et al. | |
| 6,348,911 B1 | 2/2002 | Rosenberg et al. | |
| 6,358,207 B1 | 3/2002 | Lathbury | |
| 6,385,509 B2 | 5/2002 | Das et al. | |
| 6,396,232 B2 | 5/2002 | Haanpaa et al. | |
| 6,432,112 B2 | 8/2002 | Brock et al. | |
| 6,498,944 B1 | 12/2002 | Ben-Haim | |
| 6,500,167 B1 | 12/2002 | Webster | |
| 6,522,141 B2 | 2/2003 | Debbins | |
| 6,540,685 B1 | 4/2003 | Rhoads | |
| 6,671,533 B2 | 12/2003 | Chen | |
| 6,709,667 B1 | 3/2004 | Lowe et al. | |
| 6,785,358 B2 | 8/2004 | Johnson | |
| 6,850,252 B1 | 2/2005 | Hoffberg | |
| 6,869,390 B2 | 3/2005 | Elliott et al. | |
| 6,869,396 B2 | 3/2005 | Belson | |
| 6,968,223 B2 | 11/2005 | Hanover | |
| 7,016,469 B2 | 3/2006 | Johnson | |
| 7,193,521 B2 | 3/2007 | Moberg | |
| 7,197,354 B2 | 3/2007 | Sobe | |
| 7,199,790 B2 | 4/2007 | Rosenberg et al. | |
| 7,247,139 B2 | 7/2007 | Yudkovitch | |
| 7,263,397 B2 | 8/2007 | Hauck et al. | |
| 7,276,044 B2 | 10/2007 | Ferry et al. | |
| 7,386,339 B2 | 6/2008 | Strommer | |
| 7,465,288 B2 | 12/2008 | Dudney | |
| 7,672,849 B2 | 3/2010 | Yudkovitch | |
| 7,698,966 B2 | 4/2010 | Gosselin | |
| 7,742,803 B2 | 6/2010 | Viswanathan | |
| 7,850,642 B2 | 12/2010 | Moll | |
| 7,880,717 B2 | 2/2011 | Berkley et al. | |
| 7,945,546 B2 | 5/2011 | Bliss | |
| 7,963,288 B2 | 6/2011 | Rosenberg et al. | |
| 8,317,744 B2 | 11/2012 | Kirschenman | |
| 8,317,745 B2 | 11/2012 | Kirschenman et al. | |
| 8,390,438 B2 | 3/2013 | Olson et al. | |
| 8,560,118 B2 | 10/2013 | Greer et al. | |
| 8,926,511 B2 | 1/2015 | Bar-Tal | |
| 2001/0018591 A1 | 8/2001 | Brock et al. | |
| 2001/0025183 A1 | 9/2001 | Shahidi | |
| 2002/0068868 A1 | 6/2002 | Thompson et al. | |
| 2002/0072704 A1 | 6/2002 | Mansouri-Ruiz | |
| 2002/0087048 A1 | 7/2002 | Brock et al. | |
| 2002/0184055 A1 * | 12/2002 | Naghavi et al. | 705/2 |
| 2003/0018232 A1 | 1/2003 | Elliott | |
| 2003/0050733 A1 | 3/2003 | Wang et al. | |
| 2003/0114962 A1 | 6/2003 | Niemeyer | |
| 2003/0121382 A1 | 7/2003 | Morson | |
| 2004/0050247 A1 | 3/2004 | Topping | |
| 2004/0068173 A1 | 4/2004 | Viswanathan | |
| 2004/0133189 A1 | 7/2004 | Sakurai | |
| 2004/0138530 A1 | 7/2004 | Kawai et al. | |
| 2004/0146388 A1 | 7/2004 | Khajepour et al. | |
| 2004/0193239 A1 | 9/2004 | Falwell et al. | |
| 2004/0223636 A1 | 11/2004 | Edic et al. | |
| 2004/0243147 A1 | 12/2004 | Lipow | |
| 2005/0038333 A1 | 2/2005 | Sra et al. | |
| 2005/0075538 A1 | 4/2005 | Banik et al. | |
| 2005/0172405 A1 | 8/2005 | Menkedick et al. | |
| 2005/0203382 A1 | 9/2005 | Govari et al. | |
| 2005/0222554 A1 | 10/2005 | Wallace et al. | |
| 2005/0234293 A1 | 10/2005 | Yamamoto et al. | |
| 2005/0234320 A1 | 10/2005 | Balasubramanian | |
| 2006/0052664 A1 | 3/2006 | Julian et al. | |
| 2006/0089637 A1 | 4/2006 | Werneth et al. | |
| 2006/0137476 A1 * | 6/2006 | Bull et al. | 73/862.393 |
| 2006/0155321 A1 | 7/2006 | Bressler et al. | |
| 2006/0276775 A1 | 12/2006 | Rosenberg et al. | |
| 2006/0293643 A1 | 12/2006 | Wallace et al. | |
| 2007/0016008 A1 | 1/2007 | Schoenefeld | |
| 2007/0022384 A1 | 1/2007 | Abbott | |
| 2007/0043338 A1 | 2/2007 | Moll et al. | |
| 2007/0060833 A1 | 3/2007 | Hauck | |
| 2007/0073137 A1 | 3/2007 | Schoenefeld et al. | |
| 2007/0100254 A1 | 5/2007 | Murakami et al. | |
| 2007/0120512 A1 | 5/2007 | Albu-Schaffer et al. | |
| 2007/0135803 A1 | 6/2007 | Belson | |
| 2007/0142726 A1 | 6/2007 | Carney et al. | |
| 2007/0172803 A1 | 7/2007 | Hannaford et al. | |
| 2007/0185404 A1 | 8/2007 | Hauck et al. | |
| 2007/0185485 A1 | 8/2007 | Hauck et al. | |
| 2007/0185486 A1 | 8/2007 | Hauck et al. | |
| 2007/0197896 A1 | 8/2007 | Moll | |
| 2007/0197939 A1 | 8/2007 | Wallace et al. | |
| 2007/0198008 A1 | 8/2007 | Hauck et al. | |
| 2007/0233044 A1 | 10/2007 | Wallace | |
| 2007/0233045 A1 | 10/2007 | Weitzner et al. | |
| 2007/0270685 A1 | 11/2007 | Kang et al. | |
| 2007/0276214 A1 | 11/2007 | Dachille et al. | |
| 2007/0298877 A1 | 12/2007 | Rosenberg | |
| 2008/0009791 A1 | 1/2008 | Cohen et al. | |
| 2008/0013809 A1 | 1/2008 | Zhu et al. | |
| 2008/0112842 A1 | 5/2008 | Edwards | |

(56) References Cited

U.S. PATENT DOCUMENTS

| | | |
|---|---|---|
| 2008/0201847 A1 | 8/2008 | Menkedick |
| 2008/0312536 A1 | 12/2008 | Dala-Krishna |
| 2009/0012533 A1 | 1/2009 | Barbagli |
| 2009/0033623 A1 | 2/2009 | Lin |
| 2009/0123111 A1 | 5/2009 | Udd |
| 2009/0137952 A1 | 5/2009 | Ramamurthy et al. |
| 2009/0177454 A1 | 7/2009 | Bronstein et al. |
| 2009/0192519 A1 | 7/2009 | Omori et al. |
| 2009/0195514 A1 | 8/2009 | Glynn |
| 2009/0247993 A1 | 10/2009 | Kirschenman et al. |
| 2009/0264156 A1 | 10/2009 | Burghardt |
| 2009/0322697 A1 | 12/2009 | Cao |
| 2010/0066676 A1 | 3/2010 | Kramer et al. |
| 2010/0073150 A1 | 3/2010 | Olson |
| 2010/0082039 A1 | 4/2010 | Mohr et al. |
| 2010/0256558 A1 | 10/2010 | Olson |
| 2010/0268067 A1 | 10/2010 | Razzaque et al. |
| 2010/0314031 A1 | 12/2010 | Heideman |
| 2011/0040547 A1 | 2/2011 | Gerber et al. |
| 2011/0128555 A1 | 6/2011 | Rotschild |
| 2011/0137156 A1 | 6/2011 | Razzaque |
| 2011/0152882 A1 | 6/2011 | Wenderow et al. |
| 2011/0289441 A1 | 11/2011 | Venon et al. |
| 2011/0306986 A1 | 12/2011 | Lee |
| 2012/0071891 A1 | 3/2012 | Itkowitz et al. |
| 2012/0133601 A1 | 5/2012 | Marshall et al. |
| 2012/0277663 A1 | 11/2012 | Millman et al. |
| 2013/0006268 A1 | 1/2013 | Swarup et al. |
| 2013/0154913 A1 | 6/2013 | Genc et al. |
| 2013/0165854 A1 | 6/2013 | Sandhu |
| 2013/0176220 A1 | 7/2013 | Merschon |
| 2013/0179162 A1 | 7/2013 | Merschon |

FOREIGN PATENT DOCUMENTS

| | | |
|---|---|---|
| GB | 2211280 | 6/1989 |
| GB | 2397177 | 7/2007 |
| JP | H10216238 | 8/1998 |
| JP | 2003024336 | 1/2003 |
| JP | 2007325936 | 12/2007 |
| WO | 9320535 | 10/1993 |
| WO | WO-96/39944 | 12/1996 |
| WO | WO03/049596 | 6/2003 |
| WO | WO-2006/120666 | 11/2006 |
| WO | WO-2007/088208 | 8/2007 |
| WO | WO-2007/098494 | 8/2007 |
| WO | WO-2007/120329 | 10/2007 |
| WO | WO-2007/136803 | 11/2007 |
| WO | 2007143859 | 12/2007 |
| WO | WO-2007/146325 | 12/2007 |
| WO | WO2008/045831 | 4/2008 |
| WO | 2008103212 | 8/2008 |
| WO | WO-2008/1012258 | 8/2008 |
| WO | 2009120940 | 10/2009 |
| WO | 2009120992 | 10/2009 |
| WO | WO-2009/120982 | 10/2009 |
| WO | WO-2009/120992 | 10/2009 |
| WO | 2010/025338 | 3/2010 |
| WO | 2010/059179 | 5/2010 |
| WO | 2010/068783 | 6/2010 |
| WO | 2010/107916 | 9/2010 |

OTHER PUBLICATIONS

"Supplementary European Search Report", EP 09725131 Feb. 20, 2013.

LaBelle, Kathryn, Evaluation of Kinect Joint Tracking for Clinical and In-Home Stroke Rehabilitation Tools, <http://netscale.cse.nd.edu/twiki/pub/Edu/KinectRehabilitation/Eval_of_Kinect_for_Rehab.pdf>, Dec. 2011

Padoy, Nicolas, Needle Insertion Revisted (tele-surgery in depth), (online), The John Hopkins University <URL: http://www.youtube.com/watch?v=YsY_A0kLh-g>, Jan. 2011.

Supplementary European Search Report in EP Application No. 11763450.1 (Oct. 29, 2014).

About the Kinect for Windows SDK—Microsoft Research (online), <URL: http://research.microsoft.com/en-us/um/redmond/projects/kinectsdk/about.aspx>, (actual publication date unknown).

Apple Wins Strategic Multitouch and Music Tempo Workout Patents, Patently Apple <URL: http://www.patentlyapple.com/patently-apple/2010/04/apple-wins-strategic-multitouch-music-tempo-workout-patents.html>, (actual publication date unknown).

Emotiv—Brain Computer Interface Technology (online), <URL: http://www.emotiv.com>, (actual publication date unknown).

Emotiv EPOC Software Development Kit—EPOC neuroheadset (online), <URL: http://www.emotiv.com/store/hardware/epoc/bci/epoc-neuroheadset/>, (actual publication date unknown).

International Search Report & Written Opinion, PCT/US2012/031008, Jul. 20, 2012.

International Search Report and Written Opinion, PCT/US2011/030764, Jun. 15, 2011.

Kinect—Wikipedia, the free encyclopedia (online), <URL: http://en.wikipedia.org/wiki/Kinect/>, (actual publication date unknown).

Polaris Family of Optical Tracking Systems, polaris Vicra & Spectra—Optical Measurement Systems for Medical, Northern Digital Inc. <URL: http://www.ndigital.com/medical/polarisfamily.php?act=print>, (actual publication date unknown).

The Aurora Electromagnetic Tracking System, Aurora Electromagnetic Measurement System—2D Trackinhg for Medical Guidance; Northern Digital Inc.<URL:http://www.ndigital.com/medical/aurora.pho?act=print>; (actual publication date unknown).

Wii Remote—Wikipedia, the free encyclopedia (online), <URL: http://en.wikipedia.org/wiki/Wii_Remote>, (actual publication date unknown).

International Search Report, PCT Application No. PCT/US2011/030656, Jun. 13, 2011, 8 pages.

International Search Report, PCT Application No. PCT/US2009/038525, May 27, 2009, 2 pages.

International Search Report, PCT Application No. PCT/US2009/038531, May 19, 2009, 3 pages.

International Search Report, PCT Application No. PCT/US2009/038533, Jun. 17, 2009, 2 pages.

International Search Report, PCT Application No. PCT/US2009/038618, May 22, 2009, 2 pages.

International Search Report, PCT Application No, PCT/US2009/038597, May 18, 2009, 2 pages.

International Search Report, PCT Application No. PCT/US2009/038534, May 27, 2009, 2 pages.

International Search Report, PCT Application No. PCT/US2009/038536, May 28, 2009, 2 pages.

International Search Report, PCT Application No. PCT/US2009/058121, Nov. 19, 2009, 2 pages.

Supplemental European Search Report, EP Application No. 09724550.0, Jul. 10, 2012, 6 pages.

Supplemental European Search Report, EP Application No. 09723739.0, Jul. 10, 2012, 6 pages.

Supplemental European Search Report, EP Application No. 09726364.4, Jan. 22, 2013, 7 pages.

Supplementary European Search Report for EP Application No. 11763140.5, dated Jun. 10, 2015, 7 pages.

* cited by examiner

# INTELLIGENT INPUT DEVICE CONTROLLER FOR A ROBOTIC CATHETER SYSTEM

CROSS REFERENCE TO RELATED APPLICATIONS

This application is a continuation-in-part of and claims the benefit of and priority to U.S. patent application Ser. No. 12/751,843 filed 31 Mar. 2010 (the '843 application), which is a continuation-in-part of and claims the benefit of and priority to U.S. patent application Ser. No. 12/347,811 filed 31 Dec. 2008 (the '811 application), which in turn claims the benefit of and priority to U.S. provisional patent application Nos. 61/040,143 filed 27 Mar. 2008 (the '143 application) and 61/099,904 filed 24 Sep. 2008 (the '904 application), the entire disclosure of each of the '843 application, the '811 application, the '143 application, and the '904 application are hereby incorporated by reference as though fully set forth herein.

BACKGROUND OF THE INVENTION a. Field of the Invention

This invention relates to a robotic catheter system and method for automated control of a catheter and related components, including a robotic catheter system for manipulating a catheter and related components, for example, for diagnostic, therapeutic, mapping and ablative procedures.

b. Background Art

Electrophysiology catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of conditions including irregular heart rates, loss of synchronous atrioventricular contractions and stasis of blood flow which can lead to a variety of ailments and even death.

Typically in a procedure, a catheter is manipulated through a patient's vasculature to, for example, a patient's heart, and carries one or more electrodes which may be used for mapping, ablation, diagnosis, or other treatments. Once at the intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment commonly requires precise control of the catheter during manipulation to and at the treatment site, which can invariably be a function of a user's skill level.

The inventors herein have recognized a need for a system and method for more precise and dynamic automated control of a catheter and related components, for example, for diagnostic, therapeutic, mapping and ablative procedures, that will minimize and/or eliminate procedural variability associated with an individual user's skill level. The inventors herein have also recognized a need for a system and method for performing user-specified procedures at the patient site or from a remote location.

BRIEF SUMMARY OF THE INVENTION

A robotic catheter system includes a robotic controller; a robotic manipulator; and in input controller. The input controller includes communication circuitry for receiving a signal from a user input device; memory having stored therein a device driver associated with a type of input device; and a processor configured to recognize an input device connected with the communications circuitry; load a device driver according to the recognized input device; and initialize the input device. In an embodiment, the input controller may receive an input from the input device, and translate it into a standard data format, such as, for example a format including a three-dimensional Cartesian movement. Similarly, the standard data format may include a plurality of discrete variables, and the memory of the input controller may include a program memory and a storage memory. Additionally, in an embodiment, the processor may be configured to allow a plurality of input devices to operate in a collaborative manner.

The input controller may further include an auxiliary display, to which the processor may be may be configured to provide fault messages or steering wire tension values.

DETAILED DESCRIPTION OF EMBODIMENTS OF THE INVENTION

Figure 1:
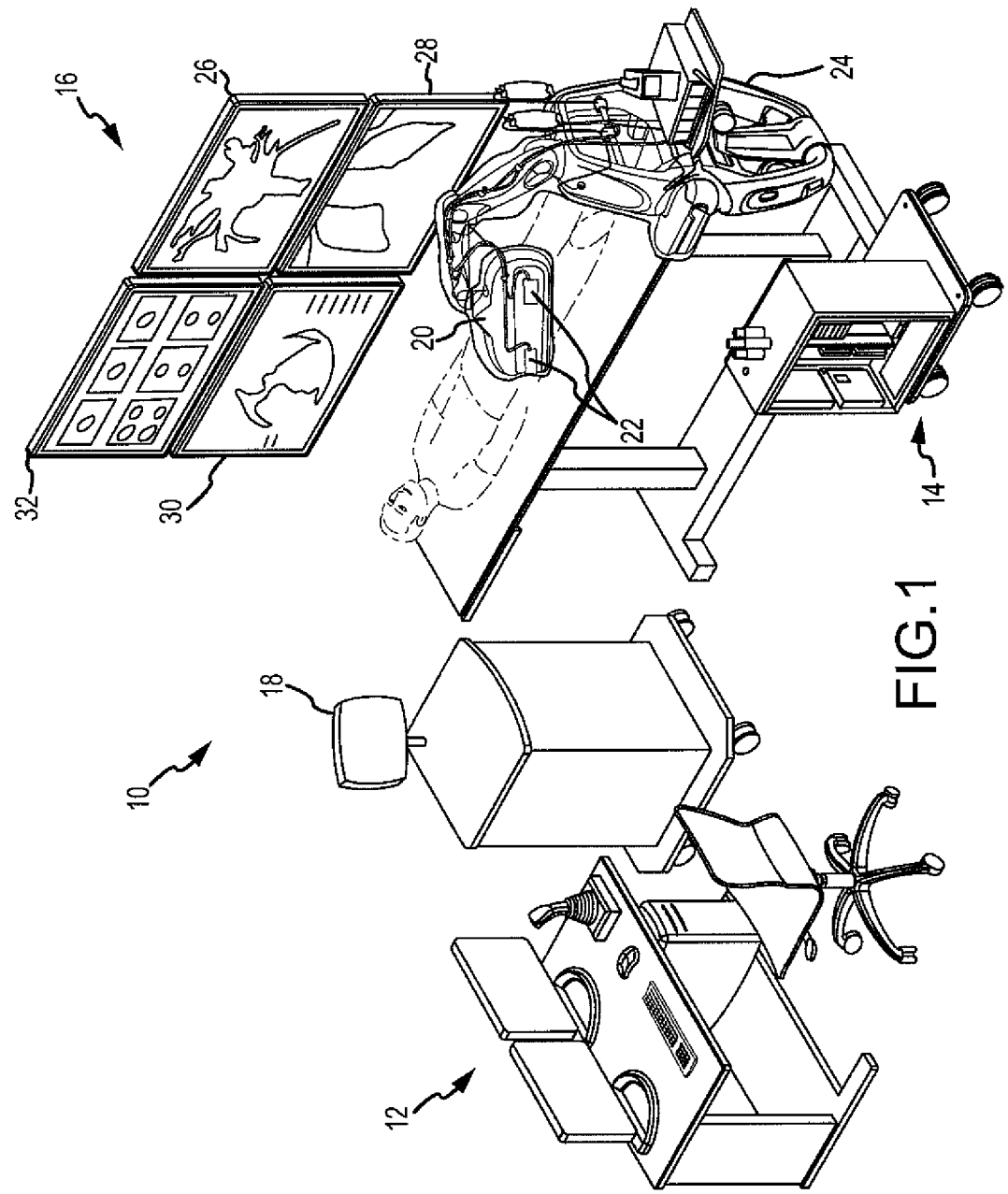
FIG. 1 is an isometric diagrammatic view of a robotic catheter system, illustrating an exemplary layout of various system components.

Referring now to the drawings wherein like reference numerals are used to identify identical components in the various views, an embodiment of robotic catheter system 10 (described in detail below), also referred to as "the system." The system may be used, for example, to manipulate the location and orientation of catheters and sheaths in a heart chamber or in another body cavity. As shown in FIG. 1 and generally described in further detail below, robotic catheter system 10 may incorporate a human input device and control system (referred to as "input control system") 12, In an embodiment, the input control system 12 may include, for example, a joystick and related controls, that a user, such as an electrophysiologist (EP) may interact with. This system 10 may additionally include an electronic control system 14 that translates motions of the user at the input device into a resulting movement of a catheter tip, and a visualization system 16 that provides a user with real-time or near-real-time positioning information concerning the catheter tip. The system may further include closed-loop feedback using an EnSite NavX system 18, commercially available from St. Jude Medical, Inc., or similar positioning systems such as, for example, the gMPS system, commercially available from Mediguide Ltd., a robotic catheter manipulator assembly 20 for operating a robotic catheter device cartridge 22 and manipulator support structure 24 (described in further detail below). The system may include similar types of controls as provided by conventional manual systems, but can provide repeatable, precise, and dynamic movements. Further detail and exemplary components of a robotic catheter system are described in detail in U.S. patent application Ser. No. 12/751,843 filed 31 Mar. 2009, and entitled "ROBOTIC CATHETER SYSTEM."

An embodiment of robotic catheter system 10 may involve automated catheter movement. A user, such as an EP, can identify locations (potentially forming a path) on a rendered computer model of the cardiac anatomy. The system can be configured to relate those digitally selected points to positions within a patient's actual/physical anatomy, and may command and control the movement of a catheter to defined positions. Once in position, either the user or system could then initiate or perform the desired treatment or therapy—which may further be in accordance with a defined algorithm. Further, such systems may enable full robotic control by using optimized path planning routines together with closed-loop position control.

Referring to FIG. 1, the input control system 12 may generally allow a user to control the movement and advancement of both a catheter and sheath. Generally, several types of input devices may be employed, including, without limitation, instrumented traditional catheter handle controls, oversized catheter models, instrumented user-wearable gloves, touch screen display monitors, 2-D input devices, 3-D input devices, spatially detected styluses, and traditional joysticks. The input device may be configured to directly control the movement of the catheter and/or sheath, or may be configured to, for example, manipulate a target or cursor on an associated display. In embodiments, for example and without limitation, the joystick may be configured for spring centering so that any movement from the center position causes an incremental movement of the actual catheter tip, or the joystick may work in absolute terms. Haptic feedback may also be incorporated to provide a user with a sense of when contact has been made.

In an embodiment, the control system 14 may include features that improve the accuracy or effectiveness of the system. Such features may include, closed-loop feedback (for example, using an EnSite NavX system or gMPS system 18) for creating realistic cardiac chamber geometries or models, displaying activation timing and voltage data to identify arrhythmias, and guiding precise catheter movement, and/or optical force transducers; active tensioning of "passive" steering wires to reduce the system response time; cumulative ablation while the tip is following a front-to-back ironing motion; and/or reactive/resistive impedance monitoring.

The visualization system 16 may provide a user with real-time or near-real-time positioning information concerning the catheter tip. In an exemplary embodiment, system 16 may include a monitor (e.g., an EnSite NavX monitor 26 or other similar monitor) for displaying cardiac chamber geometries or models, displaying activation timing and voltage data to identify arrhythmias, and/or for facilitating guidance of catheter movement. A fluoroscopy monitor 28 may be provided for displaying a real-time x-ray image or for assisting a physician with catheter movement. Additional exemplary displays may include diagnostic displays, ultrasound displays, or other reference displays (e.g., displays 30, 32).

As referenced above, EnSite NavX system 18 (described in detail in U.S. Pat. No. 7,263,397, titled "Method and Apparatus for Catheter Navigation and Location and Mapping in the Heart," incorporated by reference in its entirety) may be provided for creating realistic cardiac chamber geometries or models, displaying activation timing and voltage data to identify arrhythmias, and guiding precise catheter movement. EnSite NavX system 18 may collect electrical position data from catheters and use this information to track or navigate their movement and construct three-dimensional (3-D) models of the chamber.

In an embodiment, position data from the catheter may also be obtained using a gMPS system, commercially available from Mediguide Ltd., and generally shown and described in U.S. Pat. No. 7,386,339 entitled "Medical Imaging and Navigation System," which is incorporated herein by reference in its entirety.

As generally shown generally in FIG. 1, the robotic catheter system 10 may include one or more robotic catheter manipulator assemblies 20 that serve as the mechanical control for the movements or actions of one or more robotic catheter device cartridges 22. In an embodiment, each device cartridge may control the manipulation of an elongate catheter or sheath through a respective control mechanism. Each mechanism may be capable of independent advancement/retraction and, through controlled steering wire manipulation, may cause independent distal deflection of the catheter and/or sheath.

In an embodiment, a user (e.g., an EP) may first manually position a catheter and sheath in a coaxial arrangement within the vasculature of a patient. Once the devices are roughly positioned in relation to the heart, each device may be engaged or connected (e.g., "snapped-in") to the manipulator assembly 20.

Figure 2:
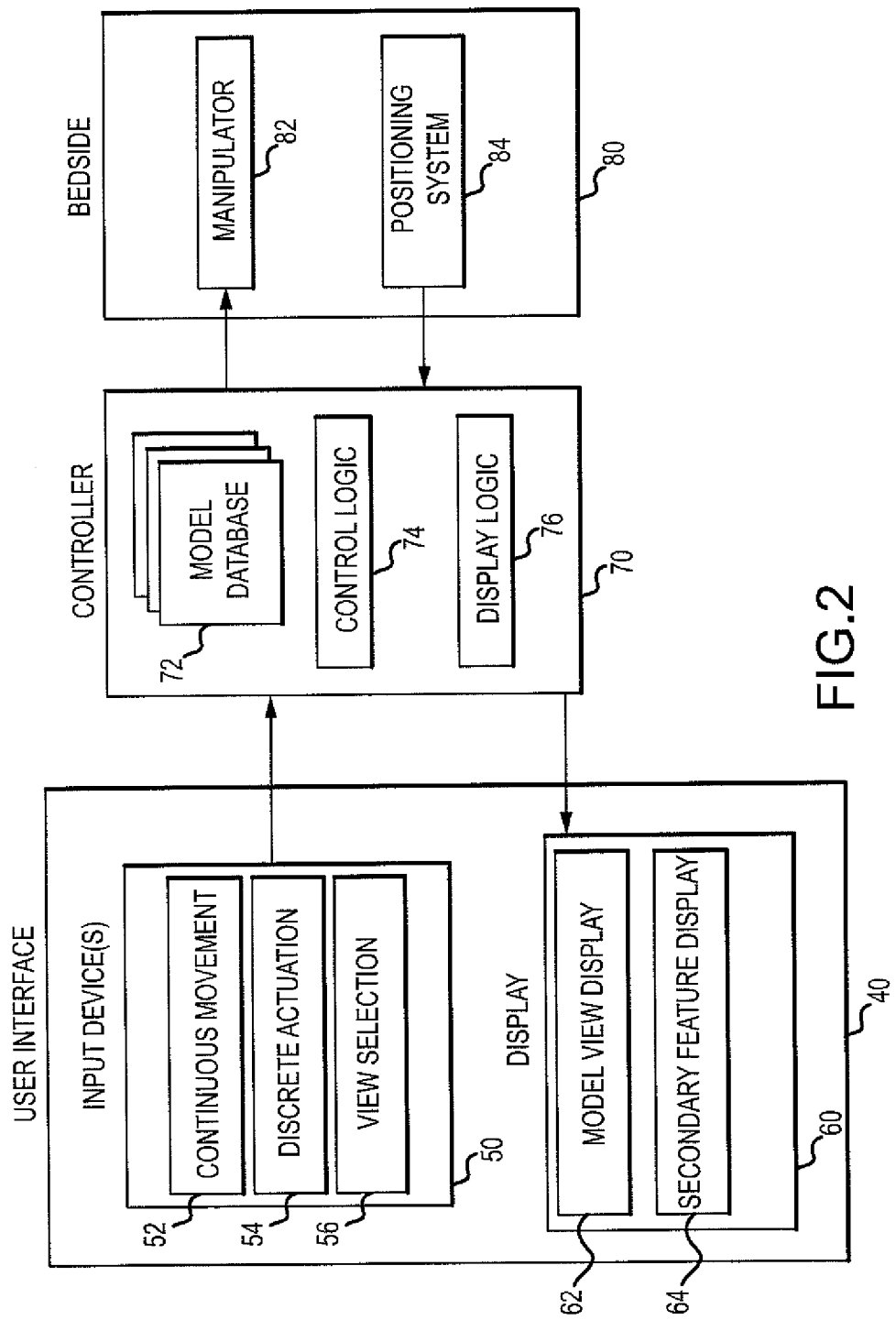
FIG. 2 is a diagram representing an embodiment of a robotic catheter system.

As schematically represented in FIG. 2, and described above, the robotic catheter system 10 generally includes three primary components: a user interface 40, a robotic controller 70, and a bedside system 80. The user interface 40 generally includes one or more input devices 50 and one or more displays 60. The controller 70 generally includes an anatomical model 72, control logic 74, and display logic 76. The bedside system 80 generally includes one or more manipulator assemblies 82, and a positioning system 84.

In an embodiment of the user interface 40, the one or more input devices 50 may be configured to receive input corresponding to a continuous movement 52 of the input device 50 and/or a discrete actuation 54 of the input device 50. The user interface may further provide a means of selecting a particular viewing perspective 56 of a three dimensional anatomical model 72. As used herein, a continuous movement input is one that can be represented on a continuous spectrum, such as the movement of a joystick, mouse, or slider. While it is understood that current digital computing operates in discrete increments, the term "continuous movement" as herein used, is intended to only distinguish from a discrete actuation, such as a button press, which must be represented as a finite state. The input device 50 is configured to provide the various forms of user input from the physician to the controller 70 for processing.

The user interface 40 may further include one or more visual displays 60 that are capable of displaying one or more views 62 of an anatomical model 72. The display 60 may further be configured to display one or more secondary features 64 either together with, or apart from, the displayed view of the model 62. In an embodiment, secondary features may include, for example, markers, targets, sliders, menu buttons, patient vital data, or other useful visual information that may not be strictly representative of the anatomical model 72. In an embodiment, the displayed view of the anatomical model may be selected 56 via the input device 50.

The controller 70 may be configured to maintain a three dimensional anatomical model 72 of the cardiac geometry, and execute both control logic 74 and display logic 76. In an embodiment, the control logic 74 can be configured to relate intended user actions into a controlled physical movement of the catheter and sheath. Such control logic may include the use of, for example, control algorithms, forward and/or inverse kinematic computations, and real-time feedback from the catheter, manipulator, or positioning system. In an embodiment, the display logic 76 may be configured to use three dimensional view rotation, translation, and/or projection techniques to present the user with a displayed representation 62 of the anatomical model 72 corresponding to the provided view selection input 56. The display logic 76 may further be configured to relate a user input 52 made with respect to a presently displayed view 62 into the coordinate system of the anatomical model.

The bedside system 80 may generally include one or more manipulator assemblies 82 configured to manipulate a catheter and sheath, and a positioning system 84 configured to detect the real-time positioning of the catheter and sheath devices within a patient.

The ability to control the ultimate motion of the catheter (via manipulator actuation) may be analytically complex because each of the input device 50, the display 60, the anatomical model 72, the manipulator 82, the distal motion of the catheter resulting from manipulator actuation 82, and the positioning system 84, may reside in different domains, potentially having different coordinate systems. As used herein, a "coordinate system" or "coordinate frame" is intended to refer a collection of variables representing controllable or perceivable qualities of an object or device. These variables may primarily include position and/or orientation, though are not necessarily defined in Cartesian space. Additionally, other temporal or environmental variables that are not strictly related to position or orientation may be included in a given coordinate system (e.g., time, breathing phase/magnitude, ECG phase/magnitude). It should also be noted that while a given unit may represent a physical distance, it may be represented in various forms, such as for example, inches, millimeters, volts, ohms, impedance, encoder counts, or other units or quantities.

Figure 3A:
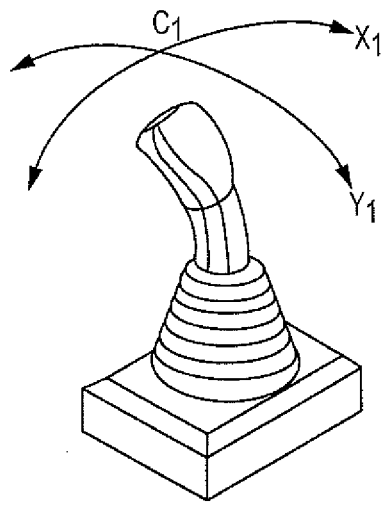
FIGS. 3a-3e illustrate exemplary coordinate systems associated with robotic catheter systems.

FIGS. 3a-3e generally illustrate several forms of coordinate systems. As illustrated in FIG. 3a, an input device, shown as a generic joystick, may operate in a first coordinate system $C_1$. As illustrated, the input coordinate system $C_1$ may include two continuous positional degrees of freedom, $\{X_1, Y_1\}$. Depending on the nature of the input device, $C_1$ may further include additional degrees of freedom meant to reflect additional motion, orientation, and/or discrete event triggers.

Figure 3B:
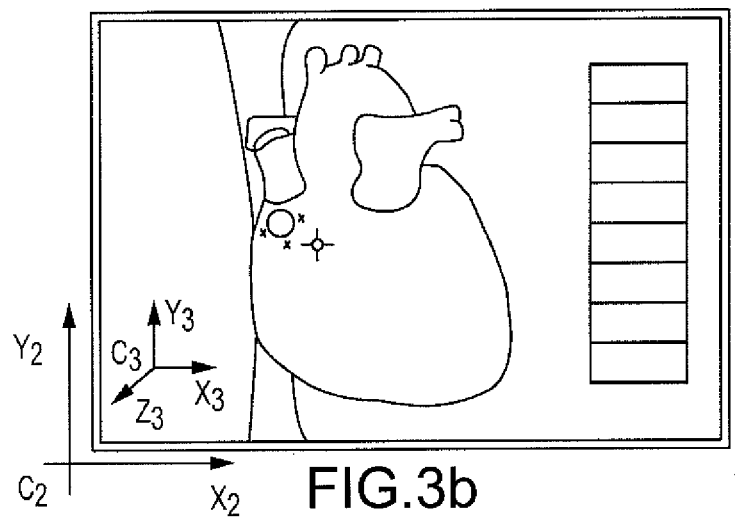
Figure 3C:
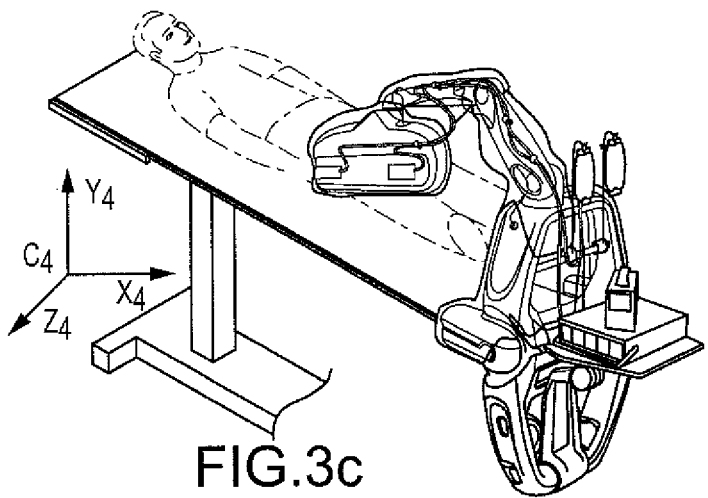
Figure 3D:
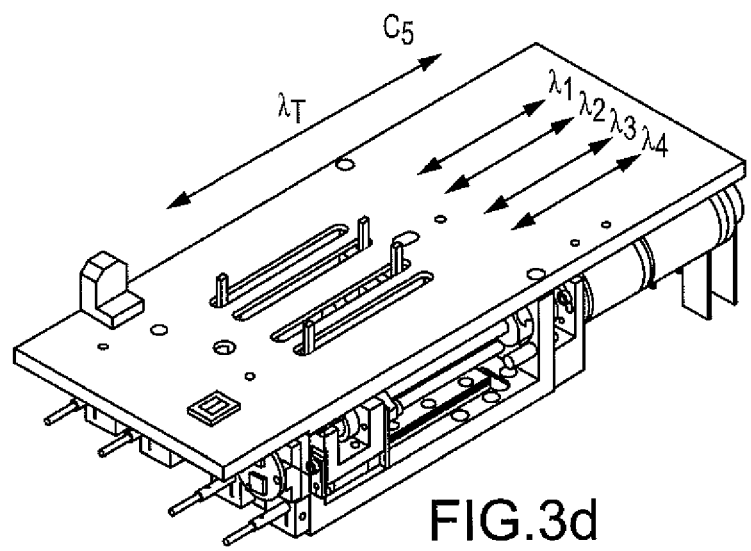

As illustrated in FIG. 3b, the display may have a second coordinate system $C_2$ that may be capable of displaying an image in two dimensional Cartesian space, $\{X_2, Y_2\}$. The computerized anatomical model representing the patient's physical anatomy may be registered in the controller as a collection points in a third coordinate system $C_3$, where each point may be defined in a three dimensional Cartesian space $\{X_3, Y_3, Z_3\}$. As generally illustrated in FIG. 3c, the actual catheter and patient anatomy may exist in a fifth coordinate frame $C_4$, that may have six degrees of freedom $\{X_4, Y_4, Z_4, \theta_4, \phi_4, \psi_4\}$ established by the positioning system, where $\{X_4, Y_4, Z_4\}$ are registered positional coordinates of a given object, and $\{\theta_4, \phi_4, \psi_4\}$ define the object's orientation in three dimensional space. As shown in FIG. 3d, a manipulator assembly may include various actuators that control the translation and/or tensioning of respective steering wires. These actuators may operate in a fourth coordinate system $C_5$, where each device cartridge has, for example, four degrees of freedom that relate to the motion of the four steering wires, and one degree of freedom that relates to the translational motion of the carriage $\{\lambda_1, \lambda_2, \lambda_3, \lambda_4, \lambda_T\}$. In two cartridge system (i.e., where the manipulator capable of independent catheter and sheath control), each cartridge may have, for example, five degrees of freedom, thus providing a manipulator with 10 total degrees of freedom $\{\lambda_1^1, \lambda_2^1, \lambda_3^1, \lambda_4^1, \lambda_T^1, \lambda_1^2, \lambda_2^2, \lambda_3^2, \lambda_4^2, \lambda_T^2\}$.

Figure 3E:
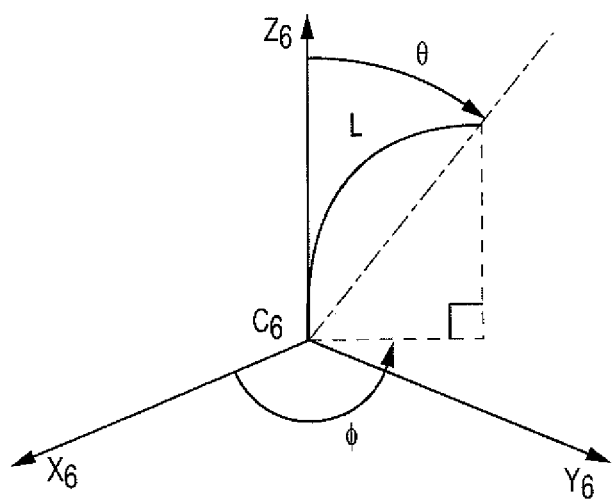

Finally, as shown in FIG. 3e, the distal motion of the catheter may be locally described in a sixth coordinate system, $C_6$, that may, for example, be located at the fulcrum point of the catheter. The distal motion within $C_6$ may be described either in a Cartesian space $\{X_6, Y_6, Z_6\}$ with the z-axis oriented along the longitudinal axis of the catheter, or in a pseudo-spherical space $\{\theta_6, \phi_6, L_6\}$. In addition to the degrees of freedom listed above, the coordinate systems of the computerized model $C_3$ and the positioning system $C_5$ may be configured to record temporal and environmental degrees of freedom, such as, for example, time, ECG phase, ECG rate, respiration rate, respiration phase, and/or respiration magnitude.

Figure 4A:
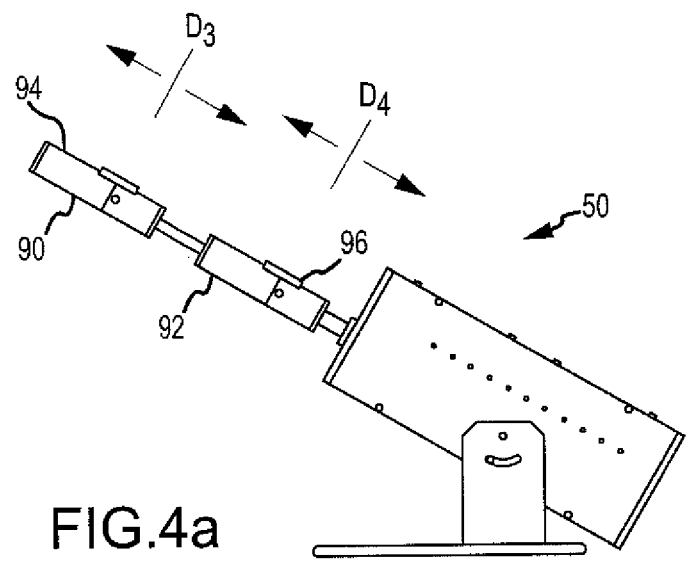
FIG. 4a is a side view of an embodiment of an exemplary input device that may be used with a robotic catheter system.
Figure 4B:
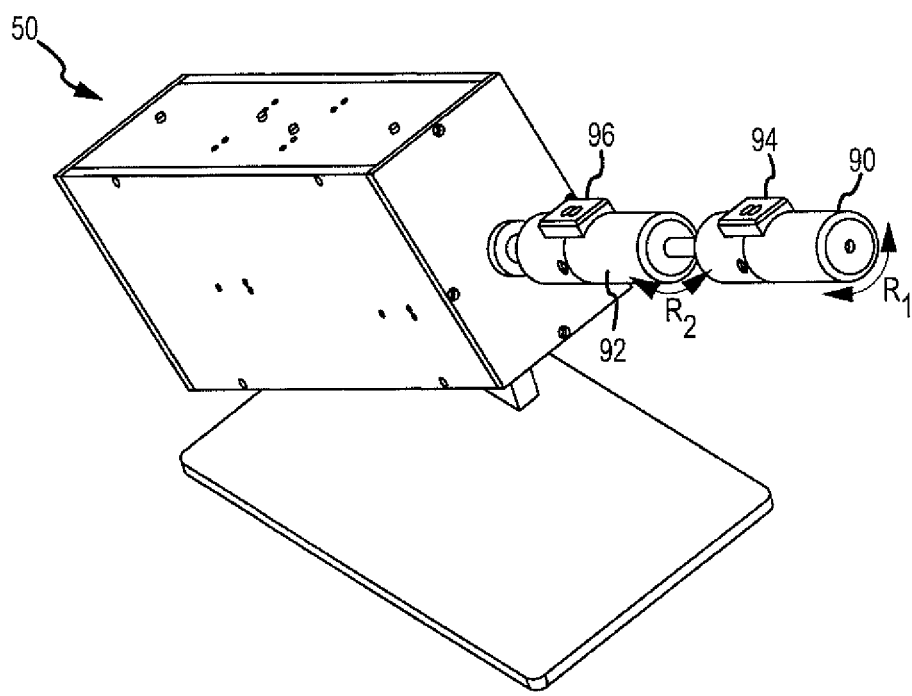
FIG. 4b is an isometric view of an embodiment of an exemplary input device that may be used with a robotic catheter system.

Referring again to FIGS. 2 and 3a, in an embodiment, the robotic catheter system 10 may include various user input devices that may each have different coordinate systems and control schemes. Various exemplary input devices are illustrated in FIGS. 4-8. In an embodiment, the interface device may allow a user to provide input to the system in a manner that mimics traditional catheter handle controls, such as generally illustrated in FIGS. 4a and 4b. In another embodiment, the user input device may be a two or three dimensional input device that can be used to spatially manipulate a displayed catheter or a displayed target. Such an interface may be akin to, for example, a traditional computer mouse, a flight joystick, a three dimensional joystick, a 3D mouse, such as those commercially available from 3Dconnexion, a Falcon joystick from Novint Technologies Inc., a touch-screen monitor, or a spatially detected stylus.

As generally shown in FIGS. 4a and 4b, an embodiment of the user input device 50 may provide instrumented sheath and catheter handles 90, 92 (or vice-versa), respectively, that are able to longitudinally translate (e.g., in directions $D_3$ and $D_4$), independently rotate (in directions $R_1$ and $R_2$), and/or include one or more movable thumb tabs (e.g., elements 94, 96). To record input, each degree of movement may be instrumented, for example, with a potentiometer or motor/encoder.

In a manner that can, if desired, mimic traditional, manual catheter control, the system may be configured such that the catheter/sheath is commanded to translate in a longitudinal direction when there a corresponding translation made with an input handle. Similarly, rotation of either handle may be configured to rotate the deflection plane of the catheter/sheath tip, and the movement of a thumb tab may cause a deflection of the catheter or sheath within in the current deflection plane.

Figure 5A:
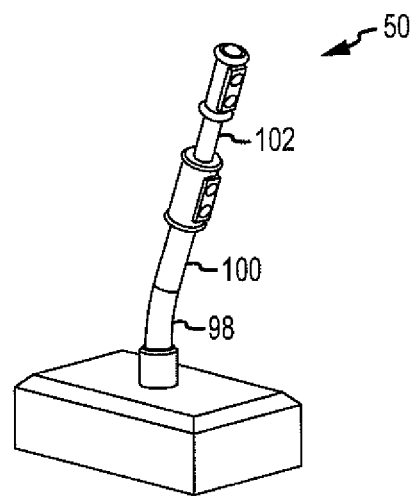
FIGS. 5a-5c are views of an embodiment of an exemplary input device that may be used with a robotic catheter system.
Figure 5B:
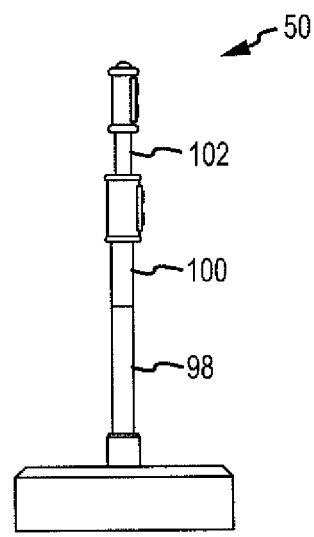
Figure 5C:
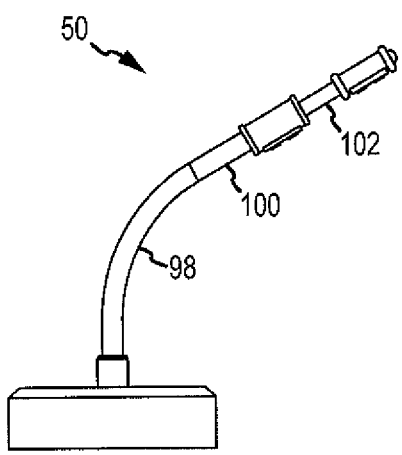

As generally shown in FIGS. 5a-5c, in another embodiment, the user interface device 50 may resemble an actual catheter. By way of example, the various sections may be constructed with pull wires, wire ducts, and variable stiffness sections 98, 100, 102, such as associated with a conventional catheter. The device may be allowed to move in a similar manner as a catheter/sheath used in an associated procedure.

In an embodiment, each movement of the input device may be monitored and used to directly control the absolute position of the actual sheath and catheter.

Figure 6A:
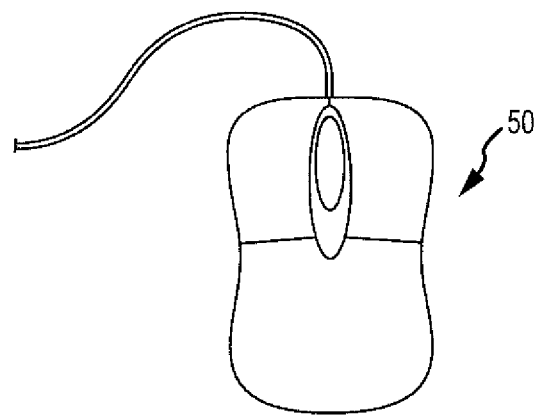
FIG. 6a is an exemplary two dimensional input device that may be used with a robotic catheter system.
Figure 6B:
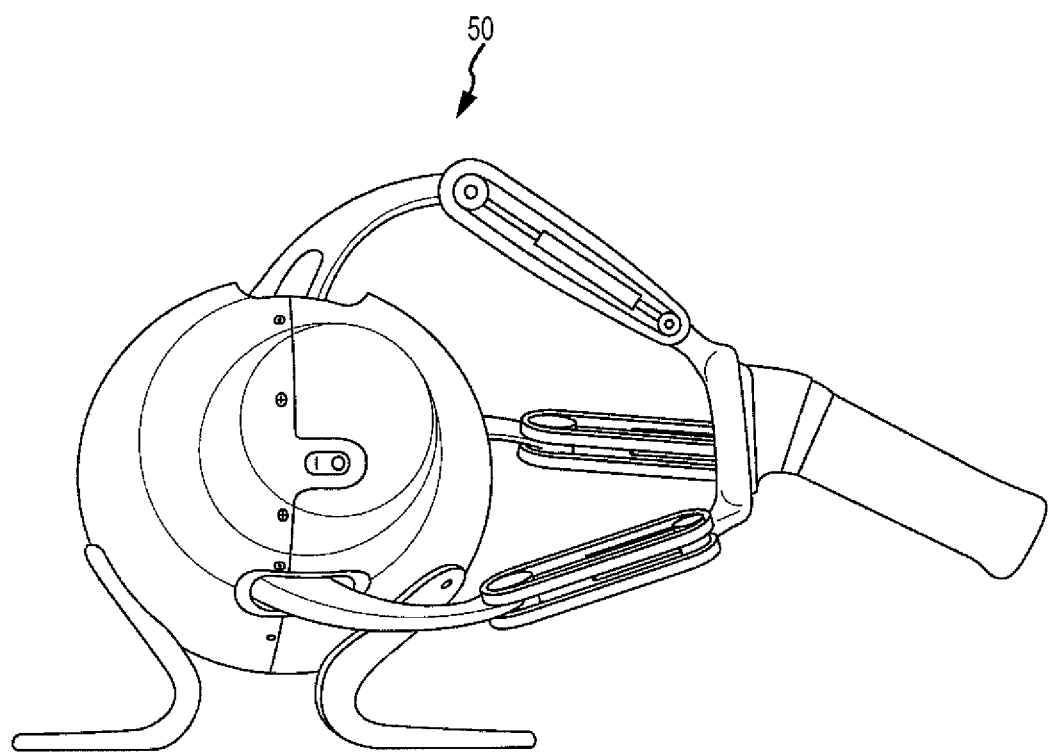
FIG. 6b is an exemplary three dimensional input device that may be used with a robotic catheter system.

As generally illustrated in FIGS. 6a, 6b, another embodiment of the user input device 50 may comprise a 2D or 3D input device, such as a mouse or 3D joystick. The recorded movement of these devices may be interpreted by the system to control the movement of the actual catheter or sheath, for example, through a display-based virtual interaction.

Figure 7A:
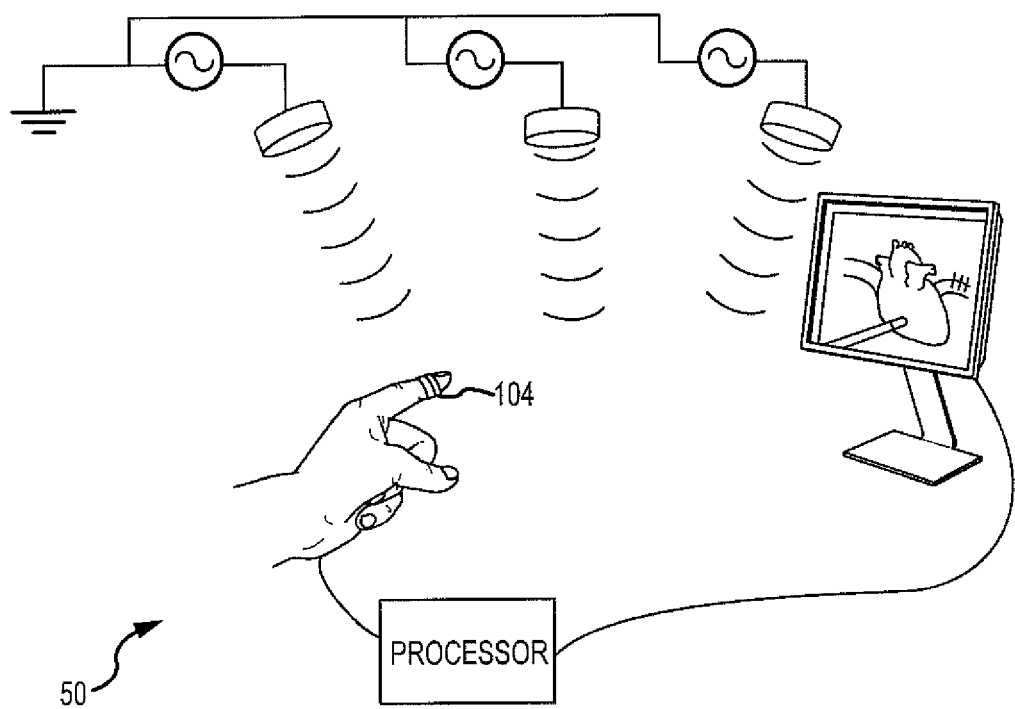
FIGS. 7a-7b are exemplary illustrations of a three dimensional input device that employs non-contact position sensing, and may be used with a robotic catheter system.
Figure 7B:
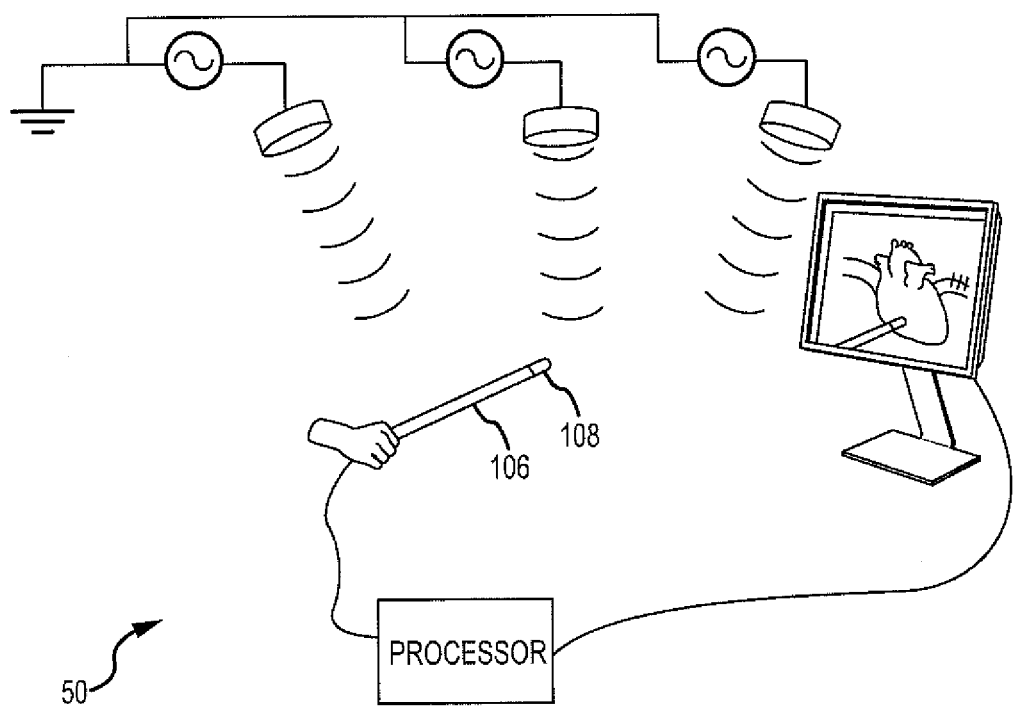

In still a further exemplary embodiment, the user input device 50 may include a spatially detected glove or stylus as generally illustrated in FIGS. 7a-7b. In an embodiment, as shown in FIG. 7a, a user's/wearer's index finger may be instrumented with various sensors 104 (e.g., position and orientation sensors, and/or accelerometers). By moving an instrumented finger, the user may manipulate the actual catheter tip. As shown in FIG. 7b, a stylus 106 may be similarly instrumented with sensors 108, and configured to measure, for example, position, orientation, and/or acceleration.

The glove or stylus input device may be locatable in 3-D space through the use of a positioning system employing a magnetic field, an electrostatic field, or through the use of an optical positioning system. These systems may include, for example, the EnSite NavX system from St. Jude Medical, the gMPS system from Mediguide, the CARTO system from Biosense Webster, the Aurora system from Northern Digital, or the RMT system from Boston Scientific.

Figure 8A:
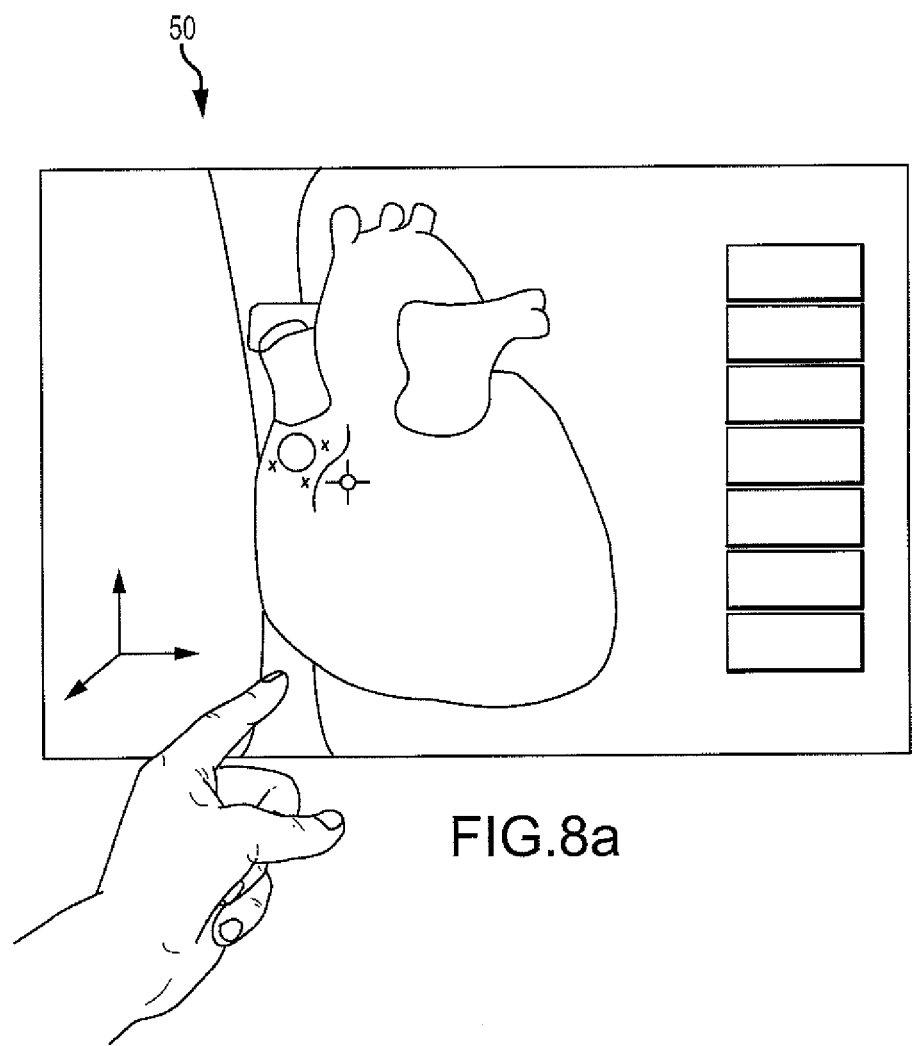
FIGS. 8a-8b are exemplary embodiments of a touch-sensitive input device that may be used with a robotic catheter system.
Figure 8B:
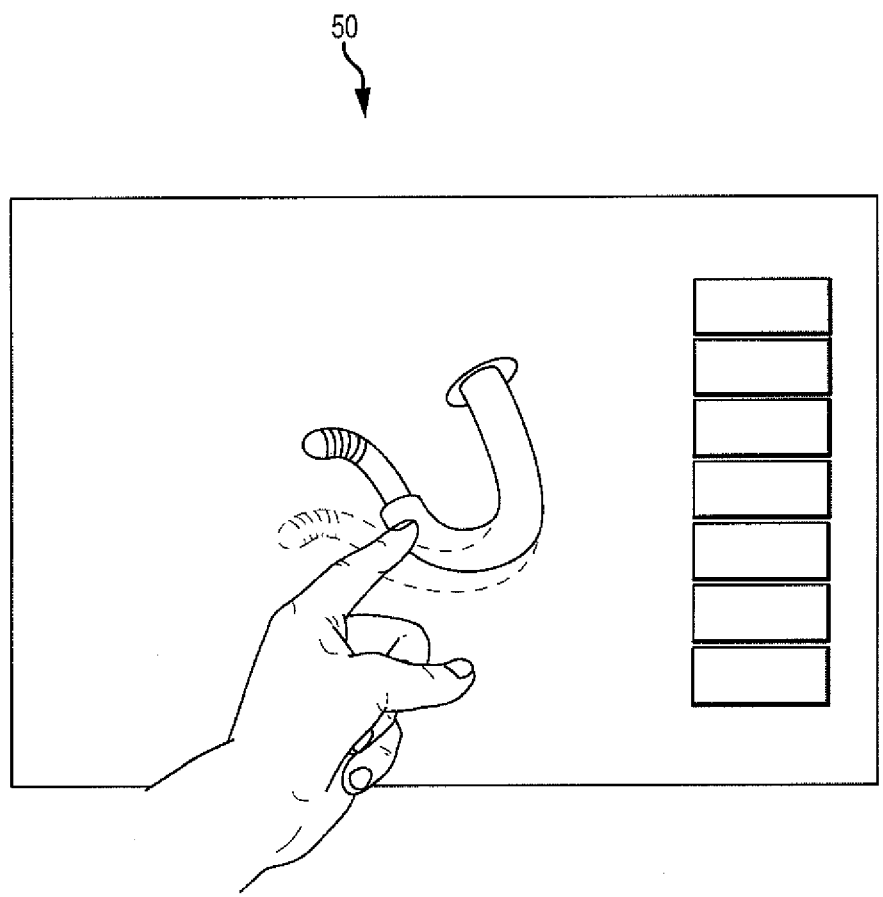

In still a further exemplary embodiment, the user interface device may be in the form of a touch screen monitor, such as generally illustrated in FIGS. 8a-8b.

Through each type of input device, the system may be further be capable of providing tactile (i.e., "haptic") feedback to the user. This type of feedback may involve forces generated by a motor connected to user interface device that a user can feel while holding or interfacing with the device. These forces may be based on actual or computed forces being applied to a physical catheter tip, and may be conveyed to the user by, for example, providing motors/encoders on each degree of freedom. While the motors may operate in a passive mode for a majority of the procedure, if feedback is required by the system, the motors may be energized to produce a torque on the input controls capable of retarding movement in particular degrees of freedom.

Figure 9:
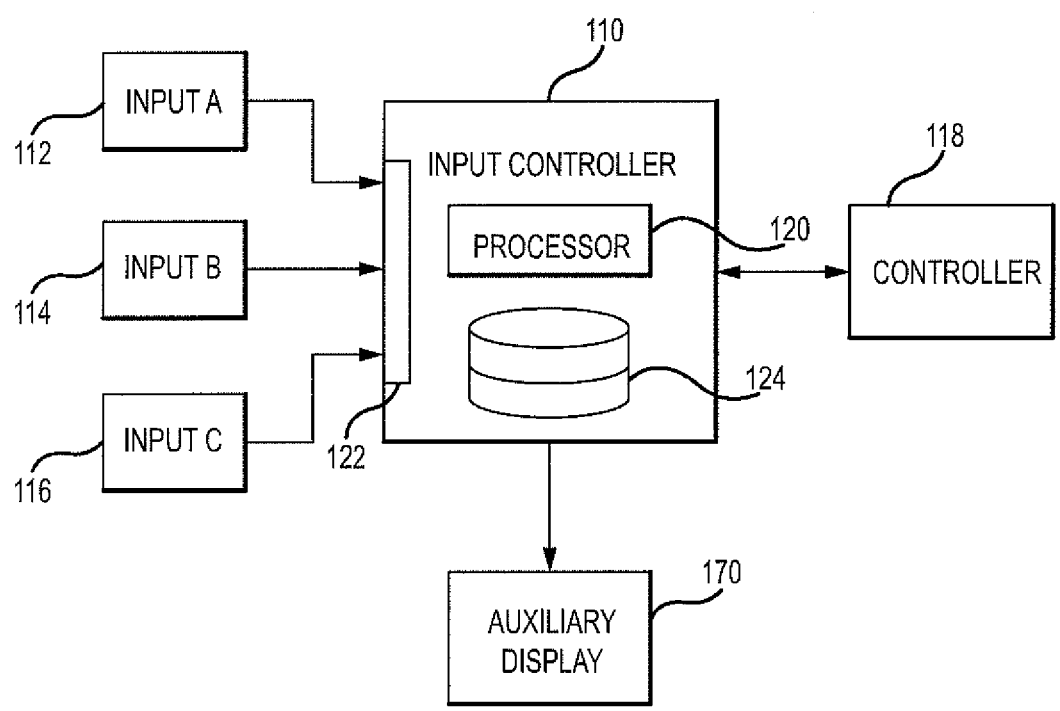
FIG. 9 is a diagram generally illustrating an input device controller with multiple input devices and an auxiliary display.

As generally illustrated in FIG. 9, in an embodiment, the robotic catheter system 10 may include an input device controller 110 that may be configured to quickly recognize and interface with one or more user input devices of varying form, design, and/or manner of operation (e.g., input devices 112, 114, 116). In the illustrated embodiment, input devices A, B, and C (respectively 112, 114, and 116) may each comprise any of the above mentioned exemplary input devices. The input controller 110 may operate to interpret the various actions of the input devices and present the intended commands to a controller 118 in a common format.

In an embodiment, the input controller 110 may include a processor 120, input communications circuitry 122, and memory 124. The communications circuitry 122 may detect the presence of one or more input devices, retrieve make and/or model information from the respective devices, and facilitate communications between the devices and the processor of the input controller 120. The input controller may additionally include memory 124 that may maintain control algorithms and device drivers for various input devices and may be used by the input controller processor 120 during the system operation. The memory 124 may include both program memory, such as random access memory (RAM), and storage memory, such as flash memory. In an embodiment, the program memory may be used during the execution of algorithms, while the storage memory may be used to maintain data and code for longer periods of time.

In an embodiment, the input controller 110 may be physically separate from the controller 118 and connected via a wired or wireless connection. In another embodiment, the two controllers may be physically integrated, though may be distinguished by function. In a further embodiment, the input controller may be integrated or provided within the one or more input devices to allow the input device to intelligently communicate raw input movements directly to the controller 118.

Figure 10:
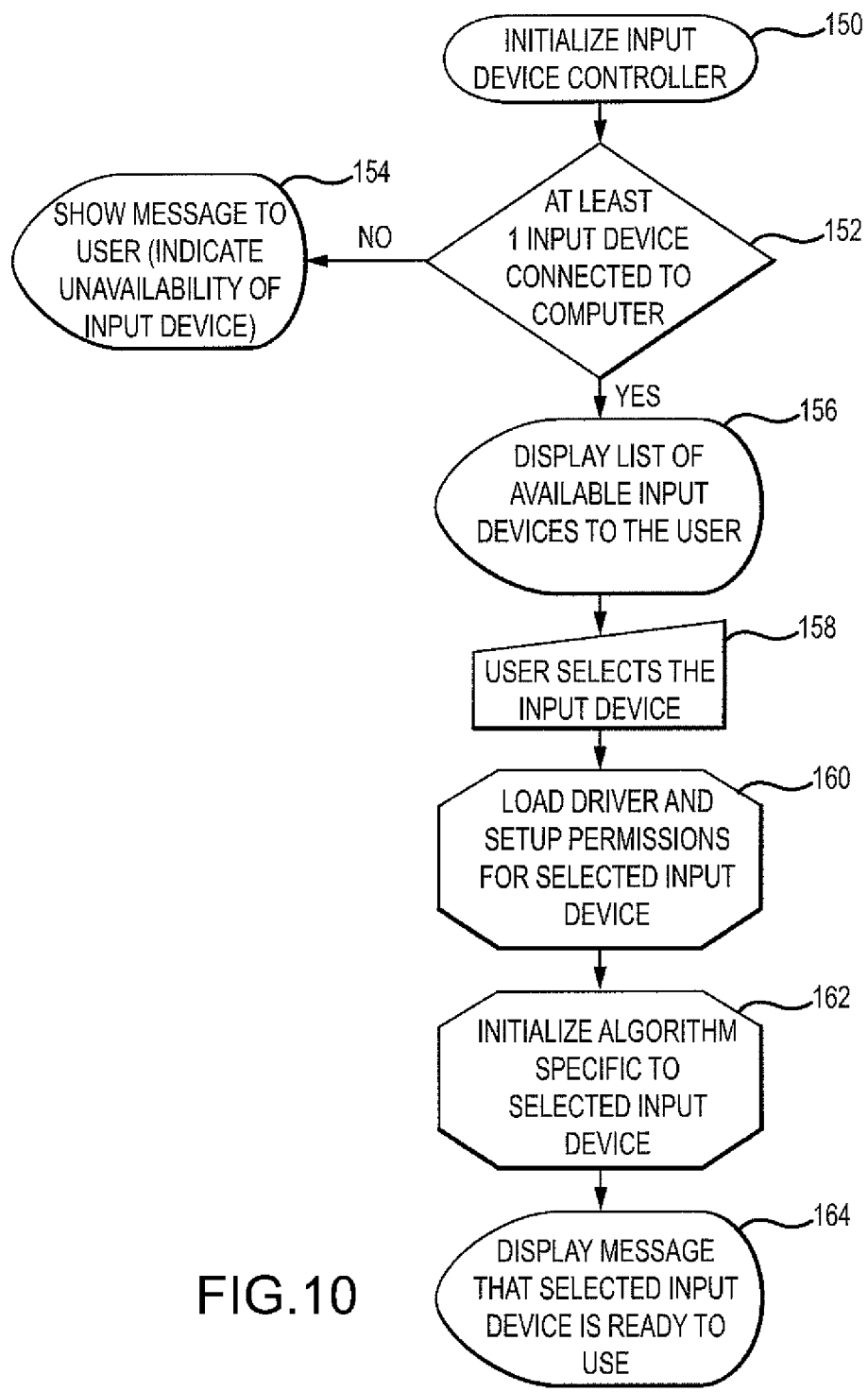
FIG. 10 is a flowchart generally illustrating the operation of an exemplary input device controller.

FIG. 10 illustrates the operation of an embodiment of the input controller 110 for setting up an input device. As shown at step 150, the controller 118 begins the operation by initializing the input device controller 110. Once initialized the input controller 110 examines the communications circuitry to determine if at least one device is connected 152. If no input device is found, the input controller 110 then may provide a corresponding alert 154 to the controller 118 and/or user.

In an embodiment, if one or more devices are connected to the input controller 110, the input controller 110 may then prompt the user (via the controller 118) to select an "active" device by first displaying a list of all connected devices to the user 156, and then by receiving an indication as to which device should be "active" 158. In another embodiment, the system may automatically determine the active device by detecting apparent movement of the device, or by monitoring hardware or software switches associated with each respective device.

Once an input device is selected as being "active," the input controller 110 may load device drivers and setup permissions that are specific to that particular device 160. The "loading" may include transferring the drivers and permissions from storage memory to program memory so they may be readily accessed during operation. For example, without limitation, the system may load either a rotary-based device driver and/or a linear-based input device driver. Some known examples of systems with rotary-based device drivers include U.S. application Ser. No. 12/150,110, filed 23 Apr. 2008 (the '110 application); and U.S. application Ser. No. 12/032,639, filed 15 Feb. 2008 (the '639 application). The '110 application and the '639 application are hereby incorporated by reference in their entirety as though fully set forth herein. Once the necessary drivers and permissions are loaded, the processor 120 of the input controller 110 may initialize one or more algorithms that are specific to the selected input device 162. The initialization may include, for example, performing startup routines for the device, performing calibration routines for the device, loading or determining device-specific parameters, or performing other initialization routines that are required for the device to operate correctly.

Once the processor 120 has executed desired or necessary initialization routines, the input controller 110 (via the controller 118) may alert the user that the input device is ready to use 164. Once initialized, input controller 110 may operate to translate the actions performed at the active input device into a standard data format that the controller 118 is configured to accept. In an embodiment, the standard data format may be a three-dimensional Cartesian position plus a plurality of discrete state-defined variables. In embodiments with a standard data format and including a plurality of discrete variables, such format and variables may linearize a desired motion vector for an input device. In another embodiment, the input controller may translate input movements into the coordinate space of the computerized anatomical model (e.g., coordinate system $C_3$). Other exemplary means of coordinate space translations are described in U.S. patent application Ser. No. 12/751,843, filed Mar. 31, 2010, and entitled "Robotic Catheter System," and which is herein incorporated by reference in its entirety.

In an embodiment, the input controller may be configured to allow multiple input devices to operate concurrently, either in a collaborative manner, or in a training/teaching environment. In a multiple input scenario, the input controller 110 may allow the user to select multiple devices and then initialize each independently. During operation, the input controller 110 may be configured to provide a single standard data signal to the controller 118, by for example intelligently merging the signals from a plurality of devices. In another embodiment, the input controller 110 may be configured to provide multiple data signals to the controller 118, where each data signal represents the input made at a respective input device. Where the input controller 110 provides multiple signals to the controller 118, each signal may be in a data format that is recognized by the controller, though need not be in an identical format as each other respective signal.

As further illustrated in FIG. 9, the input controller 110 may be provided with an auxiliary display 170. It is noted that the auxiliary display may comprise one or more forms of graphical user interfaces (GUIs). In an embodiment, the auxiliary display 170 may be configured such that the system can convey various numerical read-outs or fault messages. Exemplary numerical read-outs may include values indicative of steering wire tension, catheter distal deflection; or catheter longitudinal deflection. In an embodiment, for example, a steering wire tension value may be obtained from a strain gauge associated with a steering wire actuator within the robotic manipulator. Exemplary fault messages may include notifications that the degree of catheter or steering wire travel may be near their absolute hardware limits.

In an embodiment, the input controller 110 may record inputs to memory 124 in a sequential fashion. The input controller 110 may further be capable of replaying the movements in a visual manner on an auxiliary display 170. Additionally, if the user wishes to revert back to a previous catheter position, the input controller 110 may play back the sequential movements from memory 124 in reverse until the desired previous pose is achieved. In an embodiment, the auxiliary display 170 may also provide the user with the ability to enter various primitive commands, such as rotation, deflection, translation, and relax. Finally, the auxiliary display 170 may be capable of displaying a corporate logo or trademark, such as when no fault messages exist.

In an embodiment, an auxiliary display 170 may be may be physically associated with each of the respective input devices connected with the system. In another embodiment, the auxiliary display 170 may be an independent display that is merely provided with the system in general.

Although several embodiments of this invention have been described above with a certain degree of particularity, those skilled in the art could make numerous alterations to the disclosed embodiments without departing from the scope of this invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

The invention claimed is:

1. A robotic catheter system comprising:
a robotic controller;
a robotic manipulator; and
an input controller; the input controller including:
communication circuitry configured to receive a signal from a plurality of user input devices;
a memory including a plurality of device drivers associated with a different type of input device or a differently configured input device; and
a processor electrically coupled to the communication circuitry and to the memory, the processor configured to recognize each of the plurality of input devices configured to be connected with the communications circuitry, load a device driver according to each of the plurality of recognized input devices, and initialize the recognized input device,
wherein the input controller is further configured to prompt a user to select an active input device from the plurality of user input devices, and then detecting the active input device selected by the user; and
wherein the input control is further configured to initialize an algorithm specific to the active input device, wherein the algorithm is configured to perform a startup routine and a calibration routine for the active input device.

2. The robotic catheter system of claim 1, wherein the processor is configured to allow a plurality of input devices to operate concurrently in a collaborative manner.

3. The robotic catheter system of claim 1, wherein the processor is further configured to translate the signal from the recognized user input device into a standard data format.

4. The input controller of claim 3, wherein the standard data format includes a three dimensional Cartesian position scheme.

5. The robotic catheter system of claim 4, wherein the standard data format further includes a plurality of discrete variables to linearize a desired motion vector for the input device.

6. The robotic catheter system of claim 1, wherein the memory includes a program memory and a storage memory.

7. The robotic catheter system of claim 1, further including an auxiliary display.

8. The robotic catheter system of claim 7, wherein the processor is configured to provide fault messages to the auxiliary display.

9. The robotic catheter system of claim 7, wherein the processor is configured to provide a steering wire tension value to the auxiliary display.

10. The robotic catheter system of claim 1, further comprising an input device.

11. The robotic catheter system of claim 10, wherein the input device comprises an instrumented sheath handle and an instrumented catheter handle coupled together, wherein each of the instrumented sheath handle and the instrumented catheter handle can longitudinally translate and independently rotate.

12. The robotic catheter system of claim 10, wherein the input device comprises a three dimensional input device.

13. The robotic catheter system of claim 10, wherein the input device comprises a touch screen display.

14. The robotic catheter system of claim 1, wherein the processor is further configured to deliver an image to a graphical user interface (GUI).

15. The robotic catheter system of claim 1, wherein the processor is further configured to notify an end user.

16. The robotic catheter system of claim 1, wherein the input controller is configured to automatically determine the active input device from the plurality of user input devices by detecting movement.

17. The robotic catheter system of claim 1, wherein the input controller is configured to display a list of all connected devices.

* * * * *